US00PP15414P2

(12) United States Plant Patent
Laist

(10) Patent No.: US PP15,414 P2
(45) Date of Patent: Dec. 7, 2004

(54) ***VERBENA* PLANT NAMED 'COMIVERD'**

(50) Latin Name: *Verbena hybrida*
Varietal Denomination: Comiverd

(75) Inventor: Michal Laist, Hatamar (IL)

(73) Assignee: Cohen Nurseries, Kfar Hanagid (IL)

( * ) Notice: Subject to any disclaimer, the term of this patent is extended or adjusted under 35 U.S.C. 154(b) by 0 days.

(21) Appl. No.: 10/775,937

(22) Filed: Feb. 10, 2004

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of *Verbena* plant named 'Comiverd', characterized by its compact, mounded and cascading plant habit; freely branching habit; dense and bushy growth habit; dark green-colored leaves; and double flowers with dark red-colored petals and petaloids.

2 Drawing Sheets

Botanical classification/cultivar designation: *Verbena hybrida* cultivar Comiverd.

BACKGROUND OF THE INVENTION

The present Invention relates to a new and distinct cultivar of *Verbena* plant, botanically known as *Verbena hybrida*, and hereinafter referred to by the name 'Comiverd'.

The new *Verbena* is a product of a planned breeding program conducted by the Inventor in Bene-Zion and Kfar-Hanagid, Israel. The objective of the breeding program is to develop new *Verbena* cultivars with double flowers and attractive flower coloration.

The new *Verbena* originated from a cross-pollination made by the Inventor in February, 2001 of a proprietary selection of *Verbena hybrida* identified as code number VA-23, not patented, as the female, or seed, parent with a proprietary selection of *Verbena hybrida* identified as code number VB-3, not patented, as the male, or pollen, parent. The cultivar Comiverd was discovered and selected by the Inventor as a flowering plant from within the progeny from this cross-pollination in a controlled environment in Kfar-Hanagid, Israel in March, 2002.

Asexual reproduction of the new cultivar by terminal cuttings taken in a controlled environment in Kfar-Hanagid, Israel, since April, 2002, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Comiverd'. These characteristics in combination distinguish 'Comiverd' as a new and distinct cultivar:

1. Compact, mounded and cascading plant habit.
2. Freely branching habit; dense and bushy growth habit.
3. Dark green-colored leaves.
4. Double flowers with dark red-colored petals and petaloids.

Plants of the new *Verbena* are most similar to the parent selections. Plants of the new *Verbena* differ primarily from plants of the parent selections and cultivars known to the Inventor in flower form as plants of the parent selections and cultivars known to the Inventor have single flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Verbena*.

The photograph on the first sheet comprises a side perspective view of a typical flowering plant of 'Comiverd' grown in a container.

The photograph on the second sheet comprises a close-up view of a typical inflorescence and leaves of 'Comiverd'.

DETAILED BOTANICAL DESCRIPTION

The cultivar Comiverd has not been observed under all possible environmental conditions. The phenotype may vary somewhat with variations in environment such as temperature and light intensity without, however, any variance in genotype. The aforementioned photographs and following observations and measurements describe plants grown in Bene-Zion, Israel, under commercial practice during the spring in a polyethylene-covered greenhouse with day temperatures about 22 to 24° C., night temperatures about 16 to 18° C., and light levels about 710 lux. Cuttings were planted in 12-cm containers and grown for about three months. In the following description, color references are made to The Royal Horticultural Society Colour Chart, 1995 Edition, except where general terms of ordinary dictionary significance are used.

Botanical classification: *Verbena hybrida* cultivar Comiverd.

Parentage:

*Female, or seed, parent*.—Proprietary selection of *Verbena hybrida* identified as code number VA-23, not patented.

*Male, or pollen, parent*.—Proprietary selection of *Verbena hybrida* identified as code number VB-3, not patented.

Propagation:

*Type cutting*.—Terminal cuttings.

*Time to initiate roots, summer*.—About 9 days at 24° C.

*Time to initiate roots, winter*.—About 12 days at 20° C.

*Time to produce a rooted cutting or liner, summer*.—About 20 days at 24° C.

*Time to produce a rooted cutting or liner, winter*.—About 25 days at 20° C.

*Root description*.—Fine, fibrous; light brown in color.

*Rooting habit*.—Freely branching.

Plant description:

*Form*.—Compact, mounded and cascading plant habit.

*Growth and branching habit*.—Vigorous and freely-branching with about lateral branches potentially forming at every node; dense and bushy growth habit.

*Plant height*.—About 30 to 32 cm.

*Plant diameter or spread*.—About 40 to 42 cm.

*Lateral branches*.—Length: About 30 cm. Diameter: About 2 mm. Internode length: About 3.5 to 4.9 cm. Strength: Strong. Texture: Pubescent. Color: 147C.

*Foliage description*.—Arrangement: Opposite, simple. Length: About 3.1 to 5.6 cm. Width: About 1.3 to 2.2 cm. Shape: Narrowly ovate. Apex: Acute. Base: Attenuate with truncate tendencies. Margin: Crenate. Texture, upper and lower surfaces: Coarse, pubescent; rugose. Venation pattern: Pinnate. Color: Developing and fully expanded foliage, upper surface: 147A. Developing and fully expanded foliage, lower surface: 147B. Venation, upper surface: 147A. Venation, lower surface: 147D. Petiole: Length: About 2 to 3 mm. Diameter: About 2 mm. Color: 147D.

Flower description:

*Flower type and habit*.—Double salverform flowers arranged on terminal racemes; flowers sessile. Freely flowering with about 14 to 18 flowers per raceme. Inflorescences positioned above and beyond the foliage. Flowers last about five to seven days on the plant under greenhouse conditions. Flowers persistent.

*Fragrance*.—None detected.

*Flowering season*.—In the garden, flowering is continuous from spring until fall.

*Inflorescence height*.—About 3 to 3.4 cm.

*Inflorescence diameter*.—About 5.5 to 6.2 cm.

*Flower size*.—Diameter: About 2.6 to 2.8 cm. Length: About 2.7 to 3 cm. Throat diameter: About 4 mm. Tube diameter, at base: About 2 to 3 mm.

*Flower buds*.—Length: About 1.3 to 1.6 cm. Diameter: About 2 to 3 mm. Shape: Tubular. Color: 147A.

*Petals/petaloids*.—Quantity/arrangement: Five petals and typically about five petaloids per flower; petals fused at base. Petaloids variable in shape. Petal length: About 1.1 to 1.3 cm. Petal width: About 1.4 to 1.6 cm. Petaloid length: About 5 to 7 mm. Petal width: About 4 to 6 mm. Petal shape: Roughly cordate. Petal apex: Emarginate. Petal margin: Entire. Petal and petaloid texture, upper and lower surfaces: Velvety, smooth. Petal and petaloid color: When opening and fully opened, upper surface: 45A. When opening and fully opened, lower surface: 47C.

*Sepals*.—Quantity/arrangement: Five, fused into a tube. Calyx length: About 1.1 to 1.3 cm. Calyx diameter: About 2 to 3 mm. Texture, upper and lower surfaces: Coarse, pubescent.

*Reproductive organs*.—Stamens: Quantity per flower: Five. Anther shape: Ovoid. Anther length: Less than 1 mm; rudimentary. Anther color: Yellowish. Pollen amount: Scarce. Pollen color: Yellowish. Pistils: Quantity per flower: One. Stigma shape: Bi-parted, flattened. Stigma color: Greenish. Style length: About 2.1 to 2.2 cm. Style color: Greenish. Ovary color: Greenish.

*Seed*.—Quantity per flower: None to five. Length: About 3 to 4 mm. Diameter: Less than 1 mm. Color: Brownish.

Disease/pest resistance: Plants of the new *Verbena* have not been observed to be resistant to pathogens and pests common to *Verbena*.

Temperature tolerance: Plants of the new *Verbena* have been observed to be tolerant to temperatures ranging from 0 to higher than 35° C.

It is claimed:

1. A new and distinct cultivar of *Verbena* plant named 'Comiverd', as illustrated and described.

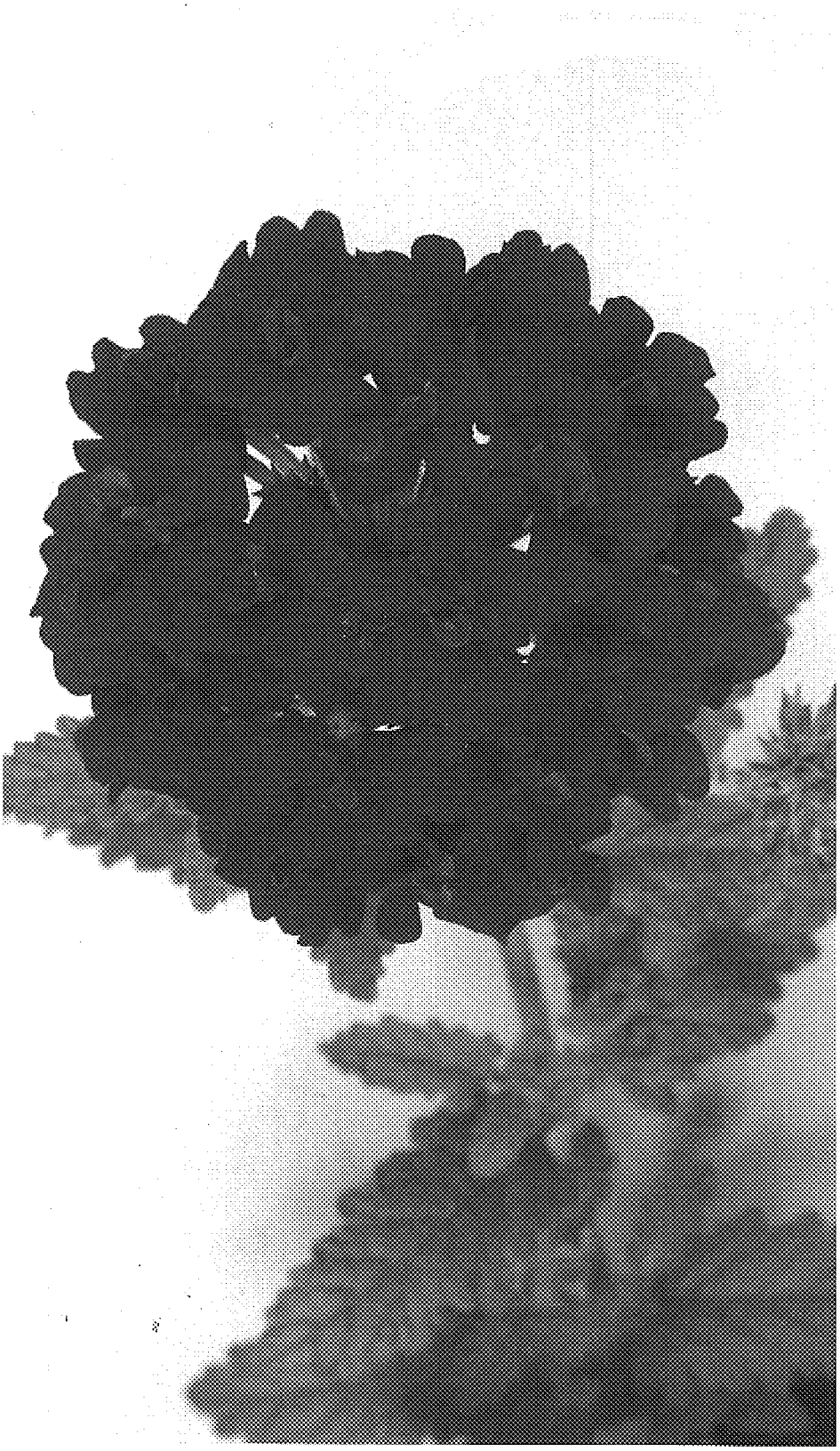

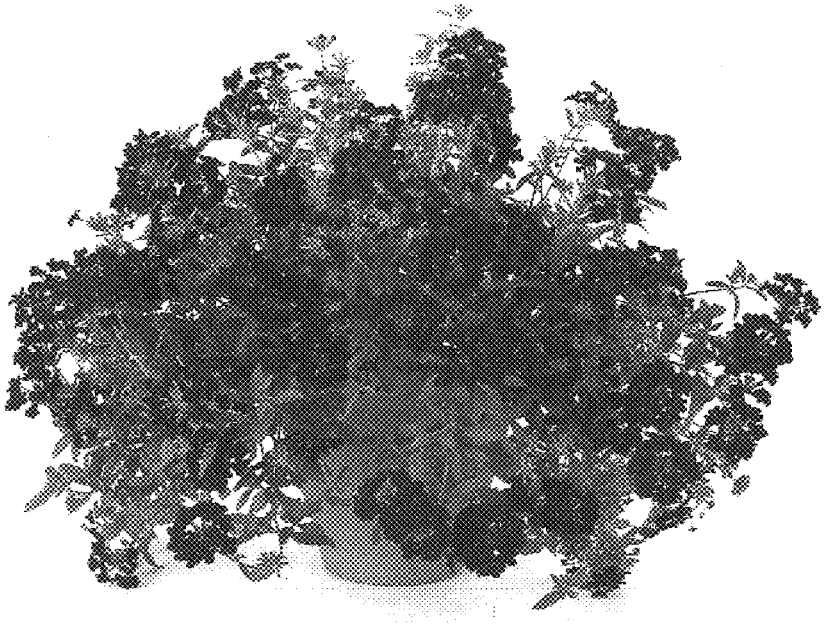

* * * * *